(12) United States Patent  
Chan et al.

(10) Patent No.: US 9,121,837 B2
(45) Date of Patent: *Sep. 1, 2015

(54) METHOD AND DEVICE FOR ENVIRONMENTAL MONITORING

(75) Inventors: Yiu Wai Chan, Shatin (HK); Sui Chun Law, Shatin (HK)

(73) Assignee: Akos Advanced Technology, Shatin (HK)

( * ) Notice: Subject to any disclaimer, the term of this patent is extended or adjusted under 35 U.S.C. 154(b) by 639 days.

This patent is subject to a terminal disclaimer.

(21) Appl. No.: 13/404,833

(22) Filed: Feb. 24, 2012

(65) Prior Publication Data

US 2012/0203461 A1     Aug. 9, 2012

Related U.S. Application Data

(63) Continuation-in-part of application No. 13/331,268, filed on Dec. 20, 2011, now abandoned, which is a continuation-in-part of application No. 12/281,824, filed as application No. PCT/CN2007/000736 on Mar. 7, 2007, now Pat. No. 8,086,407.

(30) Foreign Application Priority Data

Mar. 10, 2006    (CN) .......................... 2006 1 0057261

(51) Int. Cl.
*G01N 33/00*     (2006.01)
*G01D 21/02*     (2006.01)
(Continued)

(52) U.S. Cl.
CPC ............ *G01N 33/0032* (2013.01); *G01D 21/02* (2013.01); *G01N 33/0062* (2013.01); *G01W 1/00* (2013.01); *G01W 1/10* (2013.01)

(58) Field of Classification Search
CPC .............. G01N 33/00; G01N 33/0004; G01N 33/0031; G01N 33/0062; G01N 33/0075; G06F 19/00
USPC ......... 702/1–2, 22–24, 26–27, 30, 33, 57, 65, 702/81, 84, 99, 127–128, 130–131, 136, 702/182–183, 189; 236/44 A, 44 C, 44 R, 236/49.1–49.3; 165/58, 201, 211, 222–223, 165/248, 253, 257; 454/229, 256–258; 340/573, 628, 632–634
See application file for complete search history.

(56) References Cited

U.S. PATENT DOCUMENTS 5,261,596 A * 11/1993 Tachibana et al. ........... 236/49.3
8,086,407 B2 * 12/2011 Chan et al. ....................... 702/2
(Continued)

FOREIGN PATENT DOCUMENTS

CN           2612948 A       4/2004
CN           2646715 A      10/2004
(Continued)

OTHER PUBLICATIONS

International Search Report for International Application No. PCT/CN2007/000736, International Filing Date Mar. 7, 2007, Search Completed May 24, 2007, Mailed Jun. 7, 2007, 33 pgs.
(Continued)

*Primary Examiner* — Toan Le
(74) *Attorney, Agent, or Firm* — KPPB LLP

(57) ABSTRACT

The present invention is related to an environmental monitoring and analyzing device. The device contains a plurality of sensors, a control unit and a display unit. The different types of sensor obtain values of different environmental parameters. The control unit receives the obtained values of the environmental parameters and compares the obtained values against predetermined standards and criteria which define parameter ranges of the different environmental parameters. A display unit displays a real-time air quality report including a user-friendly interpretation of the obtained values and recommendations in response to the obtained values. By implementing this invention into an embodiment, the environmental monitoring analyzing is carried out instantly by considering the interrelationship of the obtained values of the different environmental parameters. The analyzed results are therefore much more accurate. A real-time comprehensive and easily understood by a non-technical user air quality report is provided.

25 Claims, 12 Drawing Sheets

(51) Int. Cl.
*G01W 1/00* (2006.01)
*G01W 1/10* (2006.01)

(56) References Cited

U.S. PATENT DOCUMENTS

2005/0218351 A1  10/2005  Sheng et al.
2012/0095684 A1   4/2012  Chan et al.

FOREIGN PATENT DOCUMENTS

| CN | 1737573 A | 2/2006 |
|---|---|---|
| EP | 0632268 A | 1/1995 |
| JP | 02254396 A | 10/1990 |
| JP | 05142173 A | 6/1993 |
| JP | 2003106904 A | 4/2003 |
| KR | 20060008376 A | 1/2006 |
| TW | I245891 B | 12/2005 |

OTHER PUBLICATIONS

Japanese Patent Application Examination Report for Application No. P2008-558619, dated Aug. 9, 2011, 5 pgs.
Written Opinion for International Application No. PCT/CN2007/000736, International Filing Date Mar. 7, 2007, Search Completed May 24, 2007, Mailed Jun. 7, 2007, 6 pg.

* cited by examiner

| Measured Parameter | Parameter Ranges | Message of the First Recommendation |
|---|---|---|
| Concentration of Carbon Dioxide (ppm) | 1,000 to <5,000 | Turn on air exhausting system |
| | 5,000 or above | Turn on air exhausting system<br>Decrease the number of occupants<br>Open the windows |
| Concentration of Carbon Monoxide ($\mu g/m^3$) | 10,000 to <29,000 | Turn on air exhausting system<br>Open the windows<br>Do no smoke<br>Turn off the combustion oven or device<br>Leave this place immediately |
| | 29,000 or above | Turn on air exhausting system<br>Open the windows<br>Do no smoke<br>Turn off the combustion oven or device<br>Leave this place immediately |
| Level of Respirable Suspended Particulates ($\mu g/m^3$) | 180 or above | Turn on air filtration device |
| Concentration of Total Volatile Organic Compounds ($\mu g/m^3$) | 600 or above | Turn on air filtration device |
| Temperature (°C) | >25.5 | Turn on air cooling device |
| | <20°C | Turn off air cooling device |
| | <10°C | Turn on air warming device |
| Relative Humidity (%) | <40% | Turn on humidifier |
| | >70% | Turn on dehumidifier |

Figure 9

| Message of the potential problem | First conditional array | Second conditional array | Third conditional array | Forth Conditional array |
|---|---|---|---|---|
| Pay attention to concentration of formaldehyde | i.) Temperature: 25.5 to <35°C and ii.) Level of total volatile organic compound: 600 µg/m³ above | i.) Temperature: 25.5 to <35°C and ii.) Level of total volatile organic compound: 3000 µg/m³ above | i.) Level of total volatile organic compound: 600 to <3000 µg/m³ | i.) Level of total volatile organic compound: 3000 to <25000 µg/m³ above |
| Pay attention to poor air exhausting conditions | i.) Concentration of carbon dioxide: 1,000 to <5,000 ppm | i.) Concentration of carbon dioxide: 5,000 ppm above | -- | -- |
| Pay attention to sources which irritate the eyes and the respiration system | i.) Temperature: 25.5 to <35°C and ii.) Relative humidity: 70 to 100% and iii.) Level of total volatile organic compound: 600 µg/m³ above | i.) Temperature: 25.5 to <35°C and ii.) Relative humidity: 70 to 100% and iii.) Level of total volatile organic compound: 3000 µg/m³ or above | -- | -- |
| Pay attention to the operation condition of air filtration device | i.) Relative humidity: <40% and ii.) Level of respirable suspended particulates 180 to 20,000 µg/m³ | i.) Relative humidity: <40% and ii.) Level of respirable suspended particulates 20,000 µg/m³ or above | i.) Level of respirable suspended particulates 180 to 20,000 µg/m³ | i.) Level of respirable suspended particulates 20,000 µg/m³ or above |
| Pay attention to the radon level in air | i.) Concentration of carbon dioxide: 1,000 to <5,000 ppm | i.) Concentration of carbon dioxide: 5,000 ppm or above | -- | -- |
| Pay attention to the airborne bacteria level | i.) Concentration of carbon dioxide: 1,000 to 5,000 ppm and ii.) Temperature 22 to <35°C and iii.) Relative humidity: 50 to 100% and iv.) Level of respirable suspended particulates 20 to 80 µg/m³ | i.) Concentration of carbon dioxide: 5,000 ppm above and ii.) Temperature 22 to <35°C and iii.) Relative humidity: 50 to 100% and iv.) Level of respirable suspended particulates 180 to 20,000 µg/m³ or above | i.) Concentration of carbon dioxide: 5,000 ppm above and ii.) Temperature 22 to <35°C and iii.) Relative humidity: 50 to 100% and iv.) Level of respirable suspended particulates 20,000 µg/m³ or above | -- |
| Pay attention to the number of indoor occupant | i.) Concentration of carbon dioxide: 1,000 to <5,000 ppm | i.) Concentration of carbon dioxide: 5,000 above and ii.) Level of total volatile organic compound: 600 to 3000 µg/m³ | i.) Concentration of carbon dioxide: 1,000 to <5,000 ppm above and ii.) Level of total volatile organic compound: 3000 µg/m³ above | -- |
| Pay attention to level of nitrogen monoxide | i.) Concentration of carbon monoxide: 10,000 to <25,000 µg/m³ | i.) Concentration of carbon monoxide: 25,000 µg/m³ or above | -- | -- |

Figure 10

| Message of the potential problems | Recommendation to address the potential problems |
| --- | --- |
| Pay attention to concentration of formaldehyde | Open the windows<br>Turn on air filtration device<br>Turn on air exhausting system<br>Do not smoke |
| Pay attention to poor air exhausting conditions | Open the windows<br>Turn on air filtration device<br>Decrease the number of indoor occupant |
| Pay attention to sources which irritate the eyes and the respiration system | Open the windows<br>Turn on air filtration device<br>Turn on air exhausting system<br>Decrease the number of indoor occupant<br>Turn on ventilation fan<br>Turn on dehumidifier |
| Pay attention to the operation condition of air filtration device | Turn on air filtration device<br>Turn on humidifier<br>Wear the mask |
| Pay attention to the radon level in air | Open the windows<br>Turn on air exhausting system |
| Pay attention to the airborne bacteria level | Turn on air filtration device<br>Turn on air exhausting system<br>Carry out disinfection and cleaning works<br>Wear the mask<br>Remove dust by vacuum cleaner<br>Decrease the number of indoor occupant |
| Pay attention to the number of indoor occupant | Open the windows<br>Turn on air filtration device<br>Decrease the number of indoor occupant<br>Turn on air exhausting system<br>Turn on ventilation fan |
| Pay attention to level of nitrogen monoxide | Open the windows<br>Do not smoke<br>Check the combustion oven and device<br>Leave this place immediately |

Figure 11

| Measured Parameter | Low level | Middle Low Level | Middle high Level | High Level |
|---|---|---|---|---|
| Concentration of Carbon Dioxide (ppm) | <800 (A) | 800 to <1,000 (B) | 1,000 to <5,000 (C) | 5,000 or above (D) |
| Concentration of Carbon Monoxide (µg/m³) | <2,000 (A) | 2,000 to <10,000 (B) | 10,000 to <29,000 (C) | 29,000 or above (D) |
| Level of Respriable Suspended Particulates (µg/m³) | <20 (A) | 20 to <180 (B) | 180 to <20,000 (C) | 20,000 or above (D) |
| Concentration of Total Volatile Organic Compounds (µg/m³) | <200 (A) | 200 to <600 (B) | 600 to <3,000 (C) | 3,000 or above (D) |
| Temperature (°C) | <20 (B) | 20 to <25.5 (A) | 25.5 to <30 (C) | 30 to <35 (D) |
| Relative Humidity (%) | <40 (B) | 40 to <70 (A) | 70 to <85 (C) | 85 to <100 (D) |

Figure 12

| Base on four different levels or measured parameters | Air Quality Message |
|---|---|
| Six A grades | Excellence |
| Only A grades and B grades | Good |
| Six B grades | Good |
| Only A grades, B grades, and C grades, but no D grade | Fair |
| Six C grades | Fair |
| A grades, B grades, C grades and D grades present at the same time | Poor |
| Six D grades | Poor |

Figure 13

METHOD AND DEVICE FOR ENVIRONMENTAL MONITORING

RELATED APPLICATIONS

This application is a continuation-in-part of U.S. application Ser. No. 13/331,268 filed Dec. 20, 2011, now abandoned, which application was a continuation-in-part of U.S. application Ser. No. 12/281,824, filed Sep. 5, 2008, now U.S. Pat. No. 8,086,407, which application claimed priority to Chinese application 200610057261.2, filed Mar. 10, 2006, the entire content of each of which are incorporated herein by reference.

TECHNICAL FIELD

The present invention is related to the technology of environmental monitoring. More specifically, it is related to a device and a method for environmental monitoring and analyzing.

BACKGROUND

As the problems of indoor air pollution are getting severe, the public concerns on the conditions of their living and working environment as well as the health effects by the indoor air quality are increasing. At the same time, the guidelines and the rules to control and regulate the indoor air quality have been established in different countries. Hence, the demand for instruments and equipment on monitoring the air quality is increasing.

Conventionally, there are two major types of instruments for monitoring the indoor air quality. The first type of environmental monitoring instruments is employed mainly in the research laboratories. They are of considerably large scale. The second type belongs to the portable survey type instruments and they are much more compact in size.

The results obtained by the first type of environmental monitoring instrument are highly precise and accurate. Nevertheless, the prices of this type of instruments are significantly high. The operations of these instruments are complicated and only manageable by well trained and skillful technicians.

Generally speaking, each second type environmental monitoring instrument is equipped with a sensor for measuring a particular environmental parameter. The size of this type of instrument is therefore comparatively compact. Nevertheless, as different environmental parameters are inter-correlated, the level of a single parameter is usually affected by the levels of the other parameters. To obtain the level of a particular environmental parameter with a single sensor is usually not an all-round method. The precision obtained would be low. For examples, to measure the concentration of the volatile organic compounds solely by the photo-ionization detection method may give an inaccurate result as the detection method is easily affected by the temperature and relative humidity of the environment. In addition, different types of sensors with different working principles give different outcomes when they are employed for monitoring the same environmental parameter. For these reasons, there are usually difficulties to standardize the detection methods for the environmental parameters. In order to ensure an adequate and a moderately accurate result can be obtained for a single parameter, several instruments are usually brought to site during measurement. The results obtained are then evaluated together during analysis. The measurement processes by multiple instruments are rather inconvenience.

Nevertheless, for both types of environmental monitoring instruments being mentioned, only the raw data would be simply displayed and output. None of them would provide systematically analyzed information as described in the present invention.

SUMMARY OF THE INVENTION

At least one advantage of the present invention is to address the deficiencies of current environmental monitoring devices and methods. It has the further advantage to provide a device and a method for environmental monitoring and analyzing. Different levels of the environmental parameters are detected and measured at the same time. They are then judged and analyzed systematically. A real time and comprehensive air quality report is generated. The construction of the device is simple. It is easy to be operated even by the non-technical users. The environmental parameters evaluated are highly accurate and precise.

The present invention provides a device to monitor the environment, and to solve the problems by the conventional environmental monitoring instruments. The environmental monitoring device, comprising:

a plurality of sensors being of different types, the different types of sensor obtaining values of different environmental parameters;

a control unit to receive the obtained values of the environmental parameters and to compare the obtained values against predetermined standards and criteria which define parameter ranges of the different environmental parameters; and a display unit to display a real-time air quality report comprising a simultaneous forecast to provide an instant level assessment of at least one environmental parameter not obtained by the plurality of sensors;

wherein real-time analysis of the obtained values of the different environmental parameters is performed by considering the interrelationship of the obtained values of the different environmental parameters in order to interpret the obtained values and make a recommendation based on the obtained values.

The real-time air quality report comprising a simultaneous forecast to provide an instant level assessment of at least one environmental parameter not obtained by the plurality of sensors including at least one selected from the group consisting of: formaldehyde, airborne bacteria, radon and nitrogen monoxide.

The real-time air quality report comprising a simultaneous forecast to provide an instant level assessment of at least one environmental parameter not obtained by the plurality of sensors including at least one selected from the group consisting of: formaldehyde, airborne bacteria, radon and nitrogen monoxide, carbon dioxide, carbon monoxide, respirable suspended particulates, ozone, air flow rate, fungi level, total volatile organic compounds, temperature, relative humidity, dew point, air pressure, wind speed, overall air quality.

The real-time air quality report also comprising a comment on at least one of the following: the conditions of the air exhausting conditions, the operation condition of the air filtration device, the sources which irritate the eyes and the respiration system, the number of the of indoor occupant.

The recommendation further includes the comment on the operation of at least one of the following equipment: air exhausting system, humidifier, dehumidifier, air warming device, air cooling device, air filtration device, combustion oven or device, ventilation fan, vacuum cleaner.

The recommendation further includes the comment on at least one of the following human action: to open the window, decrease the number of Occupants, leave the place immediately, not to smoke, wear a mask, carry out disinfection and cleaning works, remove dust.

At least one timer counter is included in the device for monitoring the measurement period of the plurality of sensors. The average levels of different environmental parameters by the plurality of sensors under their respective measurement periods are obtained.

The device enables the user to setup the measurement period and measurement interval for each sensor.

The device also enables the user to setup the operation condition as the operation criteria for the sensor, which based on the obtained values of the environmental parameters of the other sensor.

For example, when the carbon dioxide of heated metal oxide-type sensor is in used, pre-heating of the sensor for first 5 minutes is usually required; the values obtained in the first 5 minutes during the pre-heating status are not accurate and will not be counted for the average level of the carbon dioxide.

For example, when the radon level is to be obtained by the radon sensor, the relative humidity shall be set as below 40% for an accurate result to be obtained. The comment of setting relative humidity below 40% is an operation criterion for setting as the operation of the radon sensor.

The real-time air quality report comprising a simultaneous forecast based on the said average levels of the different environmental parameters to provide an instant average level assessment of at least one environmental parameter not obtained by the plurality of sensors.

The device also enable to user to preset the calculation and rule out criteria which is aim to eliminate any the unexpected, abnormal, out of the standard deviation of the obtained average levels of different environmental parameters by different types of sensor at any instant.

The said preset calculation and rule out criteria help to prevent inaccuracies and errors which may be introduced to the calculation during the obtaining of the average levels of the environmental parameters, which would then resulting a misleading assessment and forecasting of the environmental parameters which are not obtained by the plurality of sensors.

By the application of the preset the calculation and rule out criteria, the error of the sudden change of the values of certain environmental parameters by any unexpected disturbance can be ignored.

For example, when a woman with perfume put on walked and passed by the formaldehyde sensor or total volatile organic compound sensor which were used for measuring the concentration of formaldehyde and total volatile organic compound in the environment, the sudden rise up of the formaldehyde and total volatile organic compound can be ruled-out and be ignored based on the preset calculation and rule out criteria. These unexpected rises up of the sensor readings at a particular instant will not be counted when computing the average levels of the environmental parameters. The misleading assessment and forecasting results due to the instant rising of the values of the formaldehyde and total volatile organic compound will not be happened.

During the setup of the preset calculation and rule out criteria, the user can decide the number of sampling per sensor and the sampling time per sensor in each measurement period. The user can also decide the number of maximum and minimum sampling values which are to be ruled out during the calculation of the average level of the environmental parameters. Besides, the user can decide to employ a normal average calculation for each particular period of measurement or to employ a rolling average calculation for a long term period operation of the device.

The said setup preset calculation and rule out criteria and the setup of the said measurement period and measurement interval for each sensor can be done by user any time before or during the operation of the device. The user can input and stored the setup of the said above into the control unit of the device. The input method can be made by direct key-in through the input port or synchronized by a computer or flash memory (as indicated in the FIG. 1)

The air flow rate, heat conduction rate, disperse rate of the pollutants, pollutants emission rate, pollutant removal rate, air-change rate, and other time dependent values can further be assessed and forecasted by the device by considering:
 (1) the interrelationship of instant and/or the average level of the obtained environmental parameters; or
 (2) the interrelationship of said levels of the environmental parameters which are not obtained by the plurality of sensors; or
 (3) The interrelationship of (1) and (2) of the above;
 against the timing factor Mathematic calculations by mean of calculus and logarithms, such as integration or differentiation, log and antilog may be applied as the equations and the rules of calculations. The rules of calculations shall be preset in the control unit of the device.

For example, in the assessment of the time dependent values, the decay rate of one one environmental parameter (the pollutants) obtained by one sensor, the following equation is applied:

$$C_{ti}=C_i e^{-kti}$$

$C_{ti}$ is the pollutant concentration at the time ti, $g/m^3$
$C_i$ is the initial pollutant concentration at ti=0, $g/m^3$
k is the decay constant, $hr^{-1}$
$t_i$ is time, hr The decay constant, k, is obtained by using the linear regression on the ($\ln C_i - \ln C_{ti}$) and $t_i$ using the formula:

$$k = \frac{\sum t_i(\ln C_i - \ln C_{t_i}) - \frac{\sum t_i \sum (\ln C_i - \ln C_{t_i})}{n}}{\sum t_i^2 - \frac{(\sum t_i)^2}{n}} hr^{-1}$$

where:
 n=number of data points
 The decay rate can be calculated by $$\text{Decay rate} = Ef \times k$$

where:
Ef=a constant of environmental factor

The decay rate of the pollutants can be interpreted as:
As decay rate of pollutants is equal to the removal rate of the pollutants minus the emission/generating rate of pollutants. A positive decay rate indicate the removal rate of the pollutants is greater than the emission/generating rate of pollutants, whereas a negative result indicated that the emission/generating rate of pollutants is greater than the removal rate of the pollutants. A zero value indicated an equilibrium condition has reached where the removal rate of the pollutants is equal to the emission/generating rate of pollutants.

By interpreting the time dependent values of different environmental parameters obtained by the plurality of sensors, the following interpretation can be assessed and forecasted:
 (1) The other time dependent values of the environmental parameter which obtained by the plurality of sensors
 (2) The time dependent values of at least one environmental parameter not obtained by the plurality of sensors.

For example, in obtaining the time dependent value, the decay rate of the carbon dioxide which is obtained by the carbon dioxide sensor, the emission/generating rate by the number of occupants, and the removal rate of carbon dioxide by ventilation can be assessed and forecasted. For example, a positive decay rate of the carbon dioxide indicated that the removal rate of carbon dioxide by ventilation is higher. For example, a zero decay rate of carbon dioxide means the removal rate of carbon dioxide by ventilation is just good enough to cater the emission/generation rate by the number of occupants. In this way, the other time dependent values (the removal rate of carbon dioxide and the emission/generation rate of the carbon dioxide in this example) of the environmental parameter which obtained by the plurality of sensors can be assessed and forecasted.

For example, in an enclosed room where a zero decay rate of carbon dioxide is obtained. The result indicated that there is no emission/generating carbon dioxide as well as the removal of carbon dioxide by the ventilation is happened. The result also indicates that the other environmental pollutants such as respirable suspended particulate, formaldehyde, volatile organic compound which are generated by the ventilation means will become insignificant or even zero concentration too. Thus, in that case, if a negative value of the decay rate of the respirable suspended particulate is obtained at that moment, and if no other respirable suspended particulate removal equipment (e.g., air purifier) is in used, the emission/generation rate shall be equal to the absolute value of that negative value decay rate. Thus, by the interpretation of the interrelationship of instant and/or the average level of the obtained environmental parameters by a plurality of sensors, other time dependent values of the environmental parameter which obtained by the plurality of sensors can be assessed and forecasted.

By considering the time dependent values of some environmental parameter which the values are obtained by the plurality of sensors, the time dependent values of some environmental parameters not obtained by the plurality of sensors (e.g, airborne bacteria level, total volatile organic compounds, fungi etc) can be assessed and forecasted. For example a negative or zero decay rate of carbon dioxide with a negative decay rate of respirable suspended particulate can forecasts and tells there is a positive growing of airborne bacteria level due to (1) the poor ventilation and (2) positive generation/emission of respirable suspended particulate which serves as the nutrient source for airborne bacteria. For example a positive decay rate of carbon dioxide with a negative decay rate of volatile organic compounds can tells a very bad condition that the emission/generation rate of volatile organic compounds is too high over ventilation. The concentration of volatile organic compound is keep increasing and become too significant even within good ventilation room, the emission/generation rate of the formaldehyde can therefore forecasted to be a very high level.

At least one communication input and output port (as indicated in the FIG. 1) is included in the device. When a plurality device of the same type are connected together with the said communication input and output port, the trends of any of the air flow path, heat conduction path, disperse path of the pollutants, pollutants emission path, pollutant removal path, air-change path is forecasted and be displayed in the said a real-time air quality report.

The predetermined standards and criteria includes a first judgment principle, the first judgment principle defining at least two parameter ranges for each environmental parameter, and a corresponding recommendation for each parameter range.

The predetermined standards and criteria includes a second judgment principle, the second judgment principle defining at least one conditional array, the at least two parameter ranges defined by the first judgment principle for use as the parameter ranges for defining each conditional array, and a message corresponding to potential problems for each conditional array is provided.

The device also include a power saving function, which can work together with the power management components of the device.

When the parameter ranges of first judgment principle of the conditional array reach to the preset values, the parameter ranges of another first judgment principle which was originally consider by same said conditional array will become suppressed, hidden, ignored, and not being considered in the assessment and forecast of the environmental parameter that is not obtained by the plurality of sensors. The original conditional array will automatically shift to another conditional array. For examples, in one the conditional array, the environmental parameters of temperature and total volatile organic compound are employed for assessment of the level of formaldehyde. When the temperature is within the range of 25.5° C. to <35° C. (which is the optimal range for emission of the formaldehyde), and when the level of total volatile organic compound is 600 g/m$^3$ above, the formaldehyde level is forecasted to be a problematic and messages of this potential problem will be displayed. However, when the level of total volatile organic compound is in the range of 3000 to <25000 g/m$^3$, the reading from the temperature will become ignored in the assessment and forecast of the level of the formaldehyde. This is because the level of the total volatile organic compound is already dominant over the temperature in the assessment and forecasting of the level of formaldehyde. In indoor environment where the concentration of total volatile organic compound is in the range of 3000 to <25000 g/m$^3$, the concentration of formaldehyde is already displayed in an alert level regardless the temperature of the environment.

When the parameter ranges of said another first judgment principle which was originally considered by same said conditional array become suppressed and ignored. The sensor for obtained the parameter ranges of said another first judgment principle will be turned off automatically and temporarily for power saving. The sensor will become re-activated and the parameter ranges of the respective environmental parameter will become re-considered again at the time the parameter ranges of first judgment principle of the conditional array returned and fell back to original defined ranges.

This including this power saving function is especially beneficial for some sensors with required huge power consumptions, or sensors that needed to work with heating elements. The function helps to prevent the decay of the power source when battery or re-chargeable battery is in used, which would other affect the functioning of the device. It can help to prevent the generation of unwanted heat source or wasted heat which would affect the functions of some other sensor. It can help provide a stable and sustainable power source for all sensors of the device.

Besides, the device further comprising a recommendation to address the potential problems.

The predetermined standards and criteria includes a third judgment principle, the third judgment principle defining at least two categories for each environmental parameter, and air-quality-level judgment standards for air quality levels are defined based on the combination of different categories of the measured environmental parameters, and a message corresponding to air quality level by the air-quality-level judgment standards is provided.

The environmental parameter is any one from the group consisting of: temperature, relative humidity, volatile organic compounds, carbon monoxide, carbon dioxide, dust, ozone, carbon dioxide, radon, and formaldehyde.

The device further comprising an at least one input/output port and it is being connected to a central processing unit of at least one air treatment unit; the central processing units of the said air treatment unit receive the messages corresponding to the said real-time air quality report from the device; and based on the message to establish setting and parameter values for the operating condition of the said air treatment unit.

The said air treatment includes any unit and modules of the air equipment containing one or the combination of the components from: fan of any type, blower, pump, drawer, filtration apparatus and/or filter for air pollutants of any type, apparatus for sterilizing the air, apparatus for environmental humidity controlling, apparatus for the environmental temperature controlling, apparatus for environmental air flow controlling, apparatus for controlling environmental brightness.

The setting and parameter values for the operating condition of the said air treatment unit based on the messages corresponding to the said real-time air quality report at least one or the combination of the following:

the operating time, air flow rate, air flow path, the on and off of the air treatment unit; the on and off, the temperature setting of the apparatus for environmental humidity controlling;

the on and off of and the temperature setting of the apparatus for environmental temperature controlling;

the on and off, and power setting for the apparatus for sterilizing the air.

In another embodiment, the device is a part of the component which is being included in any unit and modules of the air equipment containing one or the combination of the components from: fan of any type, blower, pump, drawer, filtration apparatus and/or filter for air pollutants of any type, apparatus for sterilizing the air, apparatus for environmental humidity controlling, apparatus for the environmental temperature controlling, apparatus for environmental air flow controlling, apparatus for controlling environmental brightness. The control unit of the device establishes the setting and the parameter values for the operating condition of the air equipment based on the obtained values of the environmental parameters and/or the simultaneous forecast and instant level assessment of at least one environmental parameter not obtained by the plurality of sensors. In such case, the control unit of the device is included in to the central processing unit of the air equipment.

The control unit of the device comprises:
a power supply;
control circuit;
input circuits;
output circuit;
a central processing unit; and
a memory to store the predetermined standards and criteria for judging the environmental parameters, messages corresponding to interpretations, recommendations and potential problems of the parameter ranges;

the power supply and control circuit connecting an external power supply to the device;

the input circuit collecting the obtained values from the sensors and outputting them to the central processing unit;

the central processing unit analyzing the obtained values based on the predetermined standards and criteria and defining the parameter ranges of each environmental parameter, and to output the interpretation and recommendation of each parameter range for display by the display unit.

The input circuit includes an analog to digital converter and a low pulse timer.

The present invention also offers a method to monitor and analyze the environment, comprising:

obtaining values of environmental parameters;

comparing the obtained values of the environmental parameters against predetermined standards and criteria which define parameter ranges of the different environmental parameters in a control unit; and displaying a real-time air quality report from a control unit comprising a simultaneous forecast to provide an instant level assessment of at least one environmental parameter not obtained by the plurality of sensors.

wherein real-time analysis of the obtained values of the different environmental parameters is performed by considering the interrelationship of the obtained values of the different environmental parameters in order to interpret the obtained values and make recommendations based on the obtained values.

The a real-time air quality report comprising a simultaneous forecast to provide an instant level assessment of at least one environmental parameter not obtained by the plurality of sensors including at least one selected from the group consisting of: carbon dioxide, carbon monoxide, respirable suspended particulates, ozone, air flow rate, fungi level, total volatile organic compounds, temperature, relative humidity, dew point, air pressure, wind speed, overall air quality, formaldehyde, airborne bacteria, radon and nitrogen monoxide.

The real-time air quality report comprising a comment on at least one of the following: the conditions of the air exhausting conditions, the operation condition of the air filtration device, the sources which irritate the eyes and the respiration system, the number of the of indoor occupant.

The real-time air quality report further comprising messages corresponding to interpretations, recommendations and potential problems of the parameter ranges.

The real-time air quality report further comprising a user-friendly interpretation of the obtained values based on the parameter ranges.

The real-time air quality report further comprising a recommendation in response to the obtained values based on the parameter ranges that is easily understood by a non-technical user is included.

The said recommendation further includes the comment on
(i) the operation of at least one of the following equipment: air exhausting system, humidifier, dehumidifier, air warming device, air cooling device, air filtration device, combustion oven or device, ventilation fan, vacuum cleaner; and/or
(ii) at least one of the following human action: to open the window, decrease the number of occupants, leave the place immediately, not to smoke, wear a mask, carry out disinfection and cleaning works, remove dust.

The measurement period of the plurality of sensors are monitored by at least one timer counter. The average levels of different environmental parameters by the plurality of sensors under their respective measurement periods are obtained. The real-time air quality report comprising a simultaneous forecast based on the said average levels of the different environmental parameters to provide an instant average level assessment of at least one environmental parameter not obtained by the plurality of sensors is displayed.

The air flow rate, heat conduction rate, disperse rate of the pollutants, pollutants emission rate, pollutant removal rate, air-change rate, can further be assessed and forecasted by considering:

(1) the interrelationship of instant and/or the average level of the obtained environmental parameters; or
(2) the interrelationship of said levels of the environmental parameters which are not obtained by the plurality of sensors; or
(3) The interrelationship of (1) and (2) of the above;
against the timing factor.

At least one communication input and output port is used for connecting the device of the same type which employing the said environmental monitoring method together, the trends of any of the air flow path, heat conduction path, disperse path of the pollutants, pollutants emission path, pollutant removal path, air-change path is forecasted and be displayed in the said a real-time air quality report.

The method enable the user to preset calculation and rule out criteria which is aim to eliminate any the unexpected, abnormal, out of the standard deviation of the obtained average levels of different environmental parameters by different types of sensor at any instant.

The predetermined standards and criteria of the mentioned method includes a first, second and third judgment principle, the first judgment principle defining parameter ranges for the environmental parameters, corresponding recommendations for each parameter range are provided;

the second judgment principle defining conditional arrays, and at least two parameter ranges defined by the first judgment principle for use as parameter ranges for defining each conditional array, a message corresponding to potential problems and recommendations to address the potential problems for each conditional array are provided;

the third judgment principle defining at least two categories for each environmental parameter, and air-quality-level judgment standards for air quality levels are defined based on the combination of different categories of the obtained values, and a message corresponding to air quality level by the air-quality-level judgment standards is provided.

The environmental parameter is any one from the group consisting of: temperature, relative humidity, volatile organic compounds, carbon monoxide, carbon dioxide, dust, ozone, carbon dioxide, air flow rate, radon, and formaldehyde.

When the parameter ranges of first judgment principle of the conditional array reach to preset values, the parameter ranges of another first judgment principle which was originally consider by same said conditional array will become suppressed and ignored. The original conditional array will automatically shift to another conditional array.

When the parameter ranges of said another first judgment principle which was originally considered by same said conditional array become suppressed and ignored. The sensor for obtained the parameter ranges of said another first judgment principle will be turned off automatically for power saving. The sensor will become re-activated when the values of the parameter ranges being re-considered again at the time the parameter ranges of first judgment principle of the conditional array returned to original defined ranges.

In the present invention, the values of different environmental parameters are obtained by different sensors. Real-time analysis of the obtained values of the different environmental parameters is performed by considering the interrelationship of the obtained values of the different environmental parameters.

A real-time air quality report is provided. The real-time air quality report comprising a user-friendly interpretation of the obtained values and a recommendation in response to the obtained values that is easily understood by a non-technical user. (In other words, the report includes the message corresponding to the potential problems based on the parameter ranges, the recommendations to address the potential problems and the message corresponding to the air quality level.)

For certain environmental parameters, such as airborne bacteria and fungi, which need longer testing time by conventional methods They need hours for incubations by the conventional methods, the present invention would be able to provide an instant level assessment by means of forecasting, based on the (interrelationship/correlation) between different measured environmental parameters. For instance, in a warm and humid environment where the dust level has reached a certain high level (in an environment where the level of respirable suspended particulates is high), the pre-requisite conditions for growing and incubating the airborne bacteria are actually created. Based on the values of the temperature, relative humidity and level of respirable suspended particulates, the level of airborne bacteria can then be forecasted simultaneously. On another example, in an environment where the concentration of the carbon dioxide is sustained at high level, poor ventilation or too many occupants are implied. With the present invention, a user-friendly interpretation of the obtained value of the environment would be generated. The user-friendly interpretation could be the messages of recommendations such as "turn on the air exhausting system", "decrease the number of occupants", "open the windows" etc. The device by the present invention is structurally simple and low cost. The device can be handled by non-technical users easily.

The following figures and description reveal the further details of the present invention.

BRIEF DESCRIPTION OF THE DRAWINGS

FIGS. 9 to 13 depict examples of the parameter judgment standards and criteria, as well as the resulted implications.

DETAILED DESCRIPTION OF THE DRAWINGS

Figure 1:
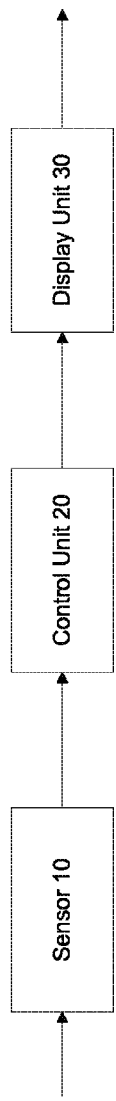
FIG. 1 illustrates circuit modules of the environmental device of the present invention.
Figure 2:
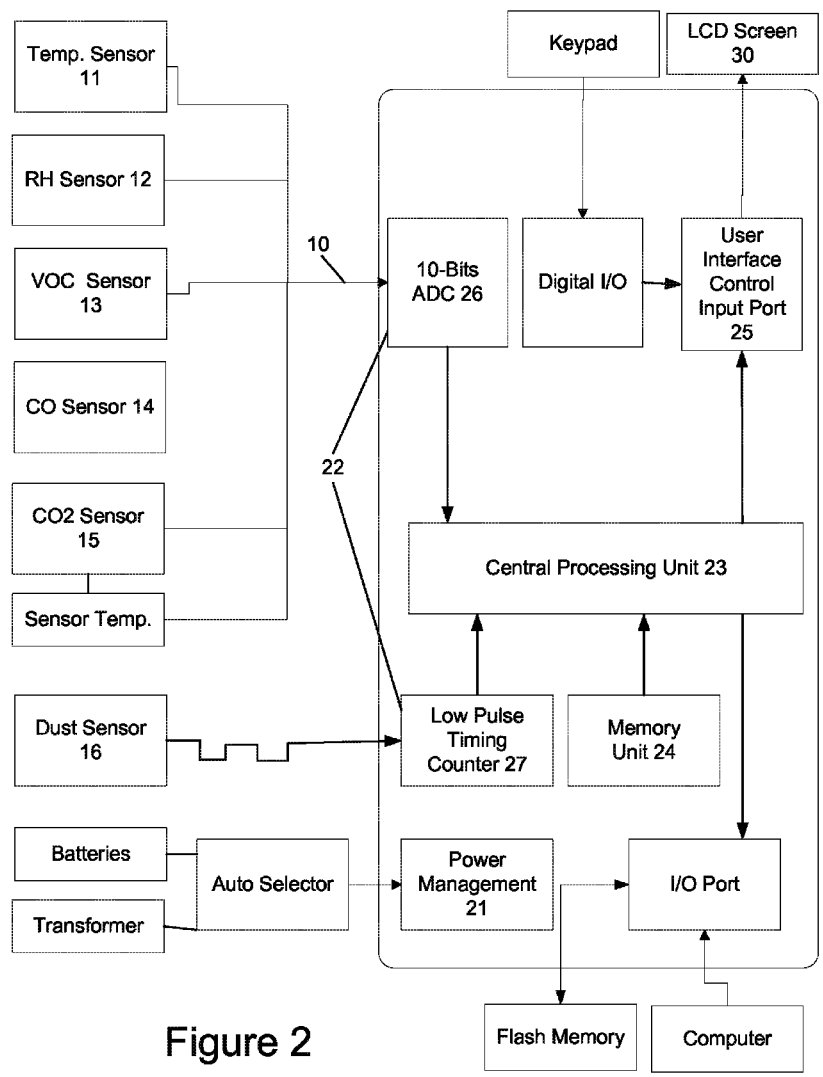
FIG. 2 depicts a block circuit diagram of the environmental device of the present invention.

Referring to FIGS. 1 and 2, the device of the present invention contains the sensors 10, the control unit 20 and the display unit 30.

The sensors 10 obtain the values of different environmental parameters. The control unit 20 collects the obtained values. In the present embodiment, the sensors 10 are a temperature sensor, a relative humidity sensor 12, a volatile organic compounds sensor 13, a carbon monoxide sensor 14, a carbon dioxide sensor 15, and a respirable suspended particulates sensor 16. Other environmental sensors such as the ozone sensor, the nitrogen dioxide sensor, the air flow rate sensor, the radon level sensor and the formaldehyde sensor can be applied for the same purpose.

Figure 3:
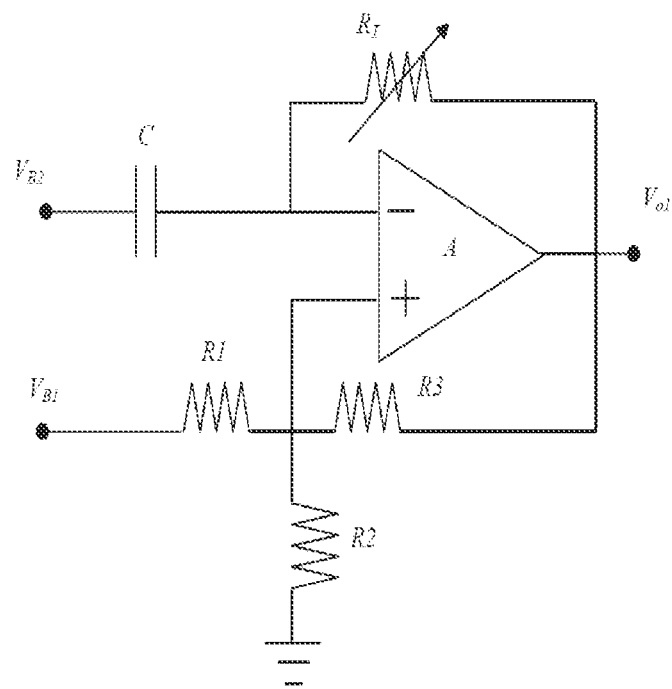
FIG. 3 depicts a circuit diagram for temperature sensor in the environmental device of the present invention.

FIGS. 3-8 indicate the circuit diagrams for the sensors in the embodiment of the present invention. The circuit for the temperature sensor 11 is shown in FIG. 3. In the present embodiment, a thermistor in which its resistance varies with the temperature is employed as the temperature sensor. The change of temperature in the environment results the change of the resistance of the thermistor $R_T$. The change of thermistor $R_T$ can be represented by the voltage output. The control unit 20 receives the output voltage Vo1. The output of the temperature sensor belongs to a chain of periodic signals, whereas the frequencies of the periodic signals are temperature dependent. The control unit 20 detects the frequency of the waveform and determines the measured temperature.

Figure 4:
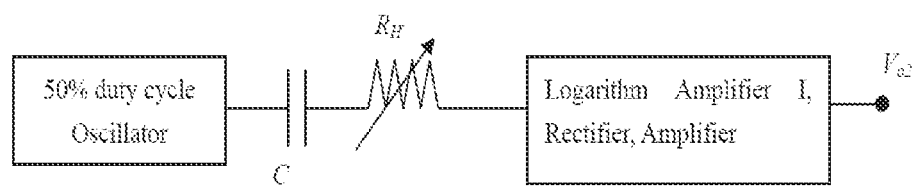
FIG. 4 depicts a circuit diagram for relative humidity sensor in the environmental device of the present invention.

FIG. 4 indicates the circuit for the relative humidity sensor 12. In the present embodiment, the relative humidity sensor 12 belongs to a resistive type relative humidity sensor. A capacitor C is connected in series to a humidity sensitive resistor $R_H$. The circuit amplifies and blocks out all DC component of the signals obtained from the sensor. The signal is output as voltage. The circuit is effective to block off the entire DC component and protect the humidity sensitive resistor $R_H$. It is a simple circuit and adaptive to different duty cycles of the input signals. In the present embodiment, a 50% oscillation duty cycle is employed.

Figure 5:
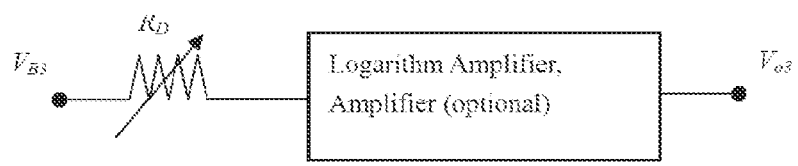
FIG. 5 depicts a circuit diagram for volatile organic compounds sensor in the environmental device of the present invention.

FIG. 5 indicates the circuit for the sensor of volatile organic compounds 13. In the present embodiment, the sensor of volatile organic compounds 13 belongs to a heated metal oxides type. The sensor varies its resistance $R_D$ with the concentration of volatile organic compounds. The input voltage $V_{B3}$ would first go through the resistor with resistance $R_D$, it will then be amplified by an analog amplifier. The voltage output is then sent to the control unit.

Figure 6:
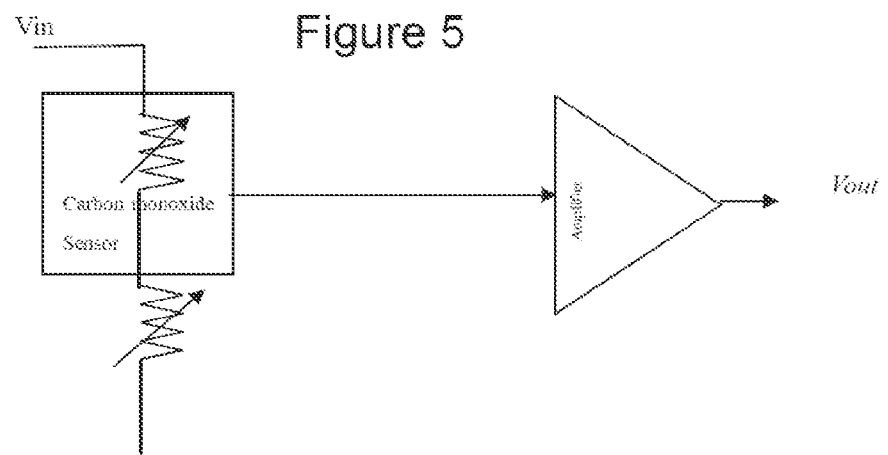
FIG. 6 depicts a circuit diagram for carbon monoxide sensor in the environmental device of the present invention.

FIG. 6 indicates the circuit for the carbon monoxide sensor 14. In the present embodiment, the carbon monoxide sensor 14 being employed belongs to a heated metal oxide type sensor. The sensor varies its resistance with the concentration of carbon monoxide. The input voltage would first go through the resistor, it will then be amplified by an analog amplifier. The voltage output is then sent to the control unit.

Figure 7:
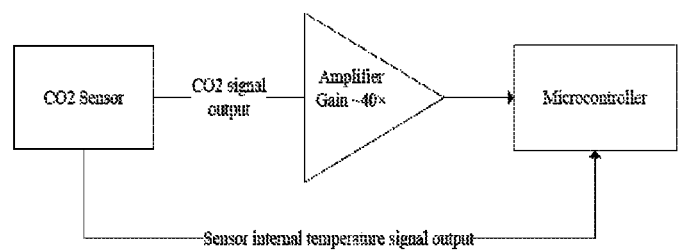
FIG. 7 depicts a circuit diagram for carbon dioxide sensor in the environmental device of the present invention.

FIG. 7 indicates the circuit of carbon dioxide sensor 15. In the present embodiment, the carbon dioxide sensor 15 belongs to a heated metal oxide type. A heating element is included in addition to the sensor element. The resistance of the sensor changes with the concentration of carbon dioxide. The input voltage first go through the resistor, it will then be amplified by an analog amplifier and be sent to the control unit 20. In order to obtain an accurate value for carbon dioxide, the desired operation temperature of the sensor is maintained by the built-in heater. The influence of the environmental temperature and ambient carbon dioxide is eliminated by comparing the voltage output obtained with that of the ambient air. A more accurate result is obtained. In addition, the internal temperature of the sensor by the heating element is fed to control unit 20. This acts as a reference for showing that the sensor has been warmed-up, and indicating that sensor has reached the optimal operation temperature.

Figure 8:
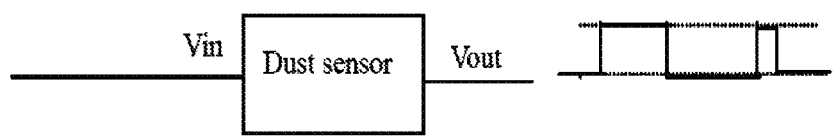
FIG. 8 depicts a circuit diagram for dust sensor in the environmental device of the present invention.

FIG. 8 indicates the circuit for the dust sensor 16 in the present embodiment. In the present embodiment, the dust sensor 16 belongs to a light scattering type sensor. The output of dust sensor will go to low voltage (ground level) when the particulate matters are detected, otherwise the output will stay at high voltage. In other words, the low pulse occupancy time is proportional to dust concentration. By obtaining the ratio of the time of total low pulse and total high pulse, the control unit 20 would be able to calculate the corresponding dust level.

The control unit 20 in the present embodiment comprises a power supply and control circuit 21, a voltage input circuit 22, a central processing unit 23, a memory unit 24 and a voltage output circuit 25. The power supply and control circuit 21 connect an external power supply to the device. The external power supply could be either AC or DC power supply. When inserting a power plug to the present embodiment, the auto power source selector directs the power source to transformer.

The voltage input circuit 22 collects the values obtained from the sensors 10. In the present embodiment, the voltage input circuit 22 includes an analog to digital converter 26 and a low pulse time counter 27. The analog to digital converter 26 receives the analogue signals from the temperature sensor 11, the relative humidity sensor 12, the volatile organic compounds sensor 13, the carbon monoxide sensor 14, and the carbon dioxide sensor 15, as well as the reference signals by the carbon dioxide sensor 15. The analog to digital converter 26 converts the analogue signals to digital signals, and inputs the digital signal into the central processing unit 23. The low pulse time counter 27 obtains the input signal from the dust sensor circuit. The central processing unit 23 collects an average value of low pulse timing from dust sensor circuit. The types of sensors employed determine the voltage input circuit. The voltage input circuit can be modified to fit with different sensors types.

The memory unit 24 stores the first judgment principle, the second judgment principle and the third judgment principle, as well as the user-friendly interpretation of the obtained values based on the parameter ranges and a recommendation in response to the obtained values based on the parameter ranges that is easily understood by a non-technical user;

The first judgment principle defines at least two-parameter ranges for each environmental parameter. The values of environmental parameter refer to the values obtained by the sensors 10, such as the values obtained by the temperature sensor, the relative humidity sensor, the volatile organic compounds sensor, the carbon monoxide sensor, the carbon dioxide sensor and the dust sensor in the present embodiment. For example, the parameter ranges for the temperature could be referred to the ranges of ">25.5° C." "<20° C." and "<10° C." etc. The second judgment principle defines at least one the conditional arrays, the at least two parameter ranges defined by the first judgment principle for use as the parameter ranges for defining each conditional array. For example, the parameter range for the temperature in an occasion is defined as "25.5-35° C." and the parameter range for the volatile organic compounds in the same occasion is defined as ">600 μg/m³". A parameter range defined by the first judgment principle can applied for defining different conditional arrays. Air-quality-level judgment standards for air quality levels are defined based on the combination of different categories of the measured environmental parameters.

The messages provided include the message corresponding to the potential problems based on the parameter ranges, the recommendations to address the potential problems and the message corresponding to the air quality level. For example, as indicated in FIG. 9, when the parameter range of temperature is defined as ">25.5° C.", the recommendation in response to the obtained values based on the parameter range is "Turn on air cooling devices". A message corresponding to potential problems for each conditional array is provided, based on the second judgment principle. Referring to FIG. 10, for example, when the temperature is in the parameter range of "25.5-35° C." and the level of the total volatile organic compounds is in the parameter range of "above 600 μg/m$^3$", the message corresponding to the potential problem for this conditional array is "high level of formaldehyde". The recommendations to address the potential problem comprise "Open the windows", "Turn on air filtration device", "Turn on air exhausting system" and "Do not smoke". FIGS. 12 and 13 indicate the air quality level, which is defined by the air-quality-level judgment standards based on the third judgment principle.

Further refer to the FIG. 10, the first conditional array showing the environmental parameters of temperature and total volatile organic compound are employed for assessment of the level of formaldehyde. When the temperature is within the range of 25.5° C. to <35° C. (which is the optimal range for emission of the formaldehyde), and when the level of total volatile organic compound is 600 g/m$^3$ above, the formaldehyde level is forecasted to be a problematic and message of this potential problem will be displayed. However, when the level of total volatile organic compound is in the range of 3000 to <25000 g/m$^3$, the reading from the temperature will become ignored in the assessment and forecast of the level of the formaldehyde. This is because the level of the total volatile organic compound is already become a dominant factor in the assessment and the forecasting of the level of formaldehyde. In indoor environment where the concentration of total volatile organic compound is in the range of 3000 to <25000 g/m$^3$, the concentration of formaldehyde is always in an alert level. In this case, the first conditional array is automatically shifted to the forth conditional array. The temperature sensor will be turned off automatically in the environmental monitoring device for power saving. When the concentration of total volatile organic compound drop back to the level of just above 600 g/m$^3$, the environmental parameter of the temperature will be re-considered again, and the forth conditional array is automatically shifted another pre-defined conditional array.

The central processing unit 23 receives the signals from the voltage input circuit 22. The voltage input circuit 22 converts all analogue signals from the sensor circuit 20 into digital signals.

The digital signals are then judged against with the predetermined standards and criteria, which are stored in the memory unit 24 under the first judgment principle defining and obtaining the parameter range. Recommendations are provided.

The obtained values are also judged against with the predetermined standards and criteria which are stored in the memory unit 24 under the second judgment principle. The second judgment principle defines the conditional arrays. At least two parameter ranges defined by the first judgment principle for use as the parameter ranges for defining each conditional array. Based on the interrelationship of the obtained values of the different environmental parameters, a message corresponding to the potential problem for the conditional array and recommendations to address the potential problems are provided.

The obtained values are also judged against with the predetermined standards and criteria which are stored in the memory unit 24 under the third judgment principle. The air-quality-level judgment standards for air quality level are defined based on the combination of different categories of the measured environmental parameters. A message corresponding to air quality level by the air-quality-level judgment standards is provided. The display unit 30 output the individual measured values and the messages by the voltage output circuit 25. The displays are in any formats, wordings, numerical, and graphical characters.

The device of the present invention contains input ports and input/output ports, whereas the input ports receive input signal from the keypad. The input/output ports transfer the information to other devices, such as computer, pocket size personal computer and flash memory. The input/output ports connect the device to other devices by an infra-red interface device, Bluetooth interface device and other wireless interface devices.

Figure 14:
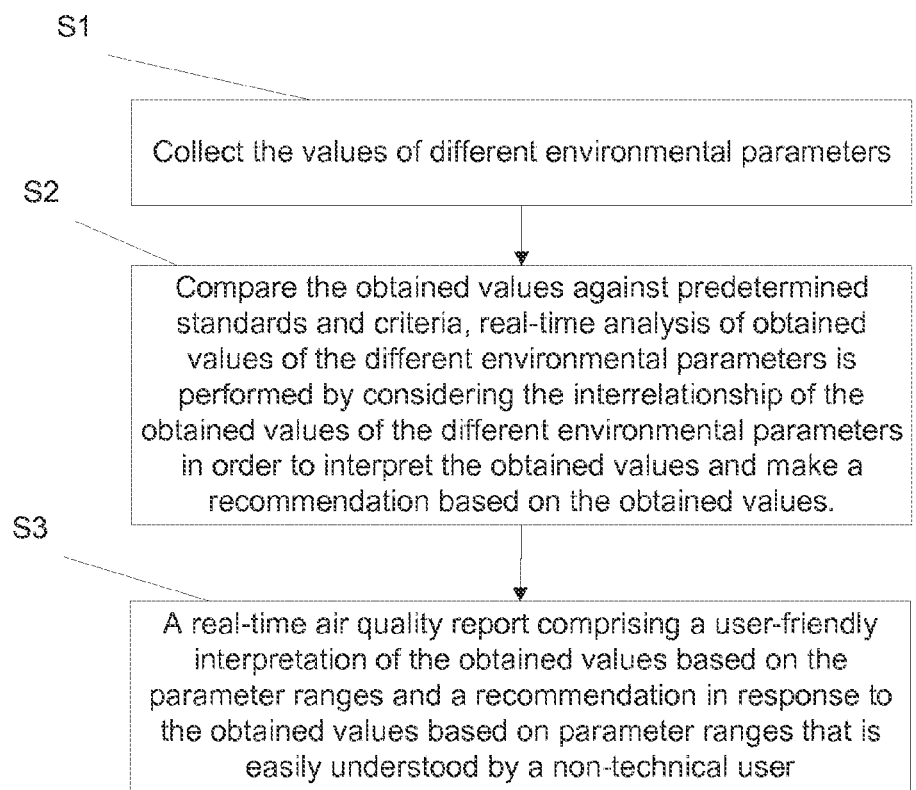
FIG. 14 depicts a flowchart of the environmental monitoring and analyzing by the present invention.

FIG. 14 indicates the method of environmental monitoring and analyzing by the present invention. The sensors S1 obtain values of different environmental parameters. The values are then sent to the control unit. The control unit in S2 compares the obtained values of the environmental parameters against the predetermined standards and criteria. Based on the interrelationship of the obtained values of the different environmental parameters, real-time analysis of the obtained values of the different environmental parameters is performed. A user-friendly interpretation of the obtained values based on the parameter ranges and recommendations in response to the obtained values based on the parameter ranges are output and displayed in the display unit S3. The first judgment principle defines the parameter ranges for each measured environmental parameter. The second judgment principle defines the conditional arrays. At least two parameter ranges defined by the first judgment principle are employed the parameter ranges for defining each conditional array. The third judgment principle defines the categories for each measured environmental parameter. An overall air quality level is defined by the air-quality-level judgment standards based on the combination of different categories of the measured environmental parameters. A message corresponding to air quality level by the air-quality-level judgment standards is provided.

Figure 15:
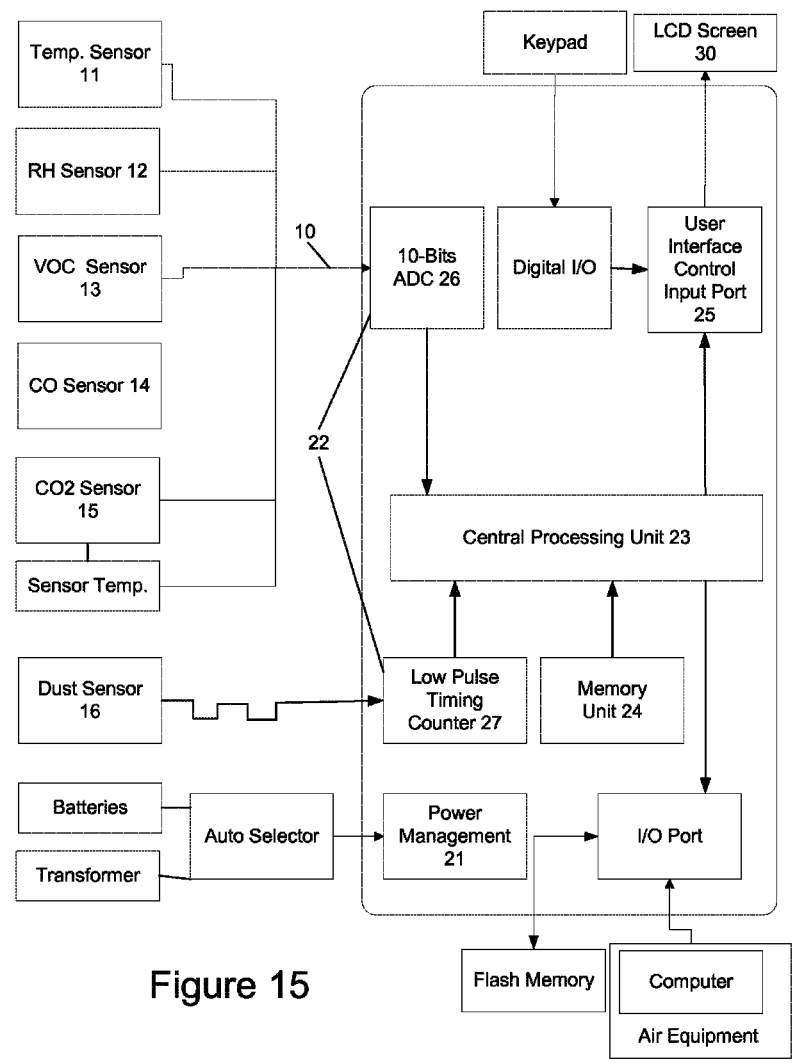
FIG. 15 depicts a block circuit diagram of the environmental device of the present invention where the input/output port is can be communicate with another computer outside the device.

Further refer to FIG. 2 and FIG. 15, the input/output port is can be communicate with another computer outside the device. In one embodiment, the said another computer is being possessed by an air treatment unit. The central processing units of the said air treatment unit receive the messages corresponding to the said real-time air quality report from the device; and based on the message to establish setting and parameter values for the operating condition of the said air treatment unit. In such case, the corresponding air treatment unit is instructed to be operated at appropriate settings or parameter values, for improving and mitigating the problematic environmental parameters accordingly, and or for prevent the forecasted problematic condition to be happened. For example, when the sensors of temperature, relative humidity, carbon dioxide and respirable suspended particulates are used for forecasting the level of the airborne bacteria level (refer to FIG. 10), and when the level of forecast is high and up to a level that the turning on the air filtration device is required (refer to FIG. 11). A message regarding this will be sent to the central processing unit of the air filtrating device directly. The central processing unit of air filtrating device will automatically instruct the air filtration device to operate at appropriate operating condition.

Figure 16:
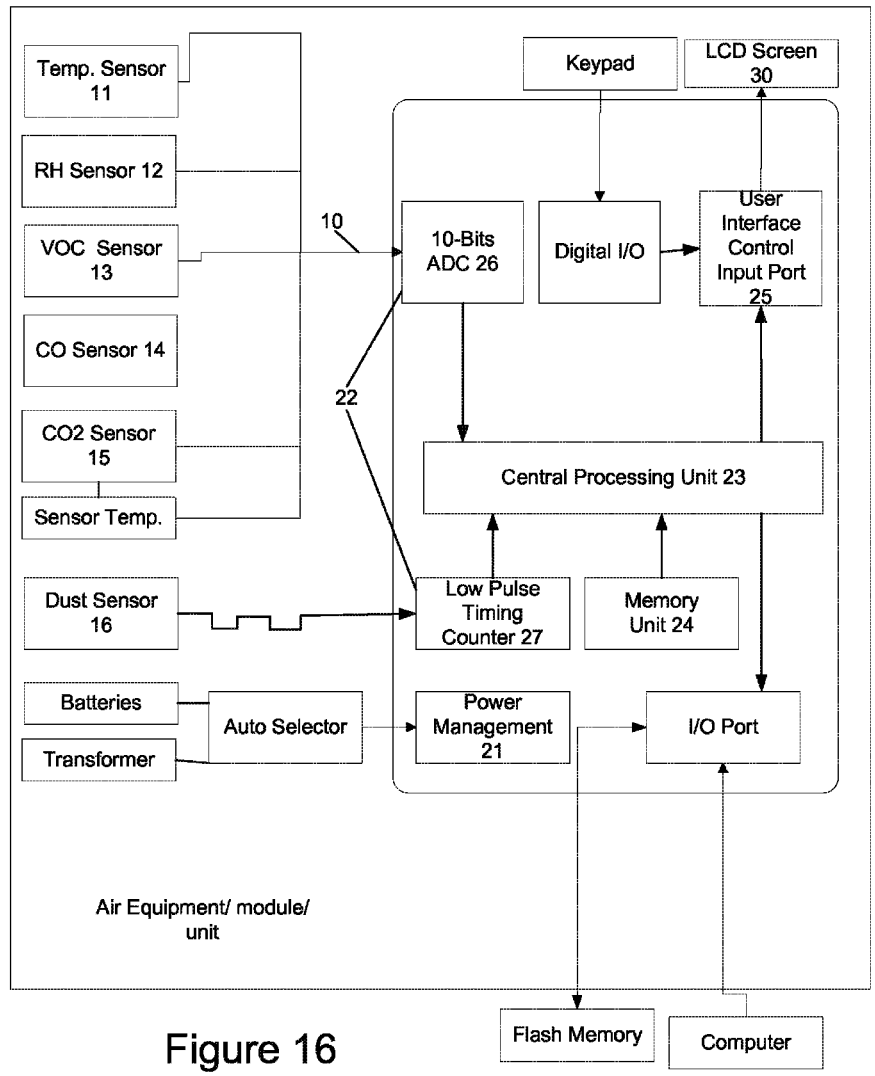
FIG. 16, the depicts a block circuit diagram of the environmental device of the present invention; wherein the device is a part of the component which is being included in any unit and modules of the air equipment.

Refer to FIG. 16, the device according to claims 1, wherein the device is a part of the component which is being included in any unit and modules of the air equipment containing one or the combination of the components from: fan of any type, blower, pump, drawer, filtration apparatus and/or filter for air pollutants of any type, apparatus for sterilizing the air, apparatus for environmental humidity controlling, apparatus for the environmental temperature controlling, apparatus for environmental air flow controlling, apparatus for controlling environmental brightness. In another words, the device is being possessed by the air equipment. The control unit of the device establishes the setting and the parameter values for the operating condition of the air equipment based on the obtained values of the environmental parameters and/or the simultaneous forecast and instant level assessment of at least one environmental parameter not obtained by the plurality of sensors.

The invention claimed is:

1. An environmental monitoring device, comprising:
    a plurality of sensors of different types, where the different types of sensor obtain values of different environmental parameters;
    a control unit to receive the obtained values of the different environmental parameters and to compare the obtained values against predetermined standards and criteria which define parameter ranges of the different environmental parameters;
    a display unit to display a real-time air quality report comprising a simultaneous forecast to provide an instant level assessment of at least one environmental parameter not obtained by the plurality of sensors;
    wherein real-time analysis of the obtained values of the different environmental parameters is performed by considering the interrelationship of the obtained values of the different environmental parameters in order to interpret the obtained values and make a recommendation based on the obtained values.

2. The environmental monitoring device according to claim 1, wherein the real-time air quality report comprises a simultaneous forecast to provide an instant level assessment of at least one environmental parameter not obtained by the plurality of sensors including at least one selected from the group consisting of: formaldehyde, airborne bacteria, radon and nitrogen monoxide, carbon dioxide, carbon monoxide, respirable suspended particulates, ozone, air flow rate, fungi level, total volatile organic compounds, temperature, relative humidity, dew point, air pressure, wind speed, and overall air quality.

3. The environmental monitoring device according to claim 1, wherein the real-time air quality report comprising: at least one selected from the group consisting of:
    a comment on at least one of the group consisting of: conditions of air exhaust, an operation condition of the air filtration device; sources which irritate eyes and a respiration system, a number of the indoor occupants, and messages corresponding to interpretations;
    a recommendation on the operation of at least one piece of equipment selected from the group consisting of: an air exhausting system, a humidifier, a dehumidifier, an air warming device, an air cooling device, an air filtration device, a combustion oven, a combustion device, a ventilation fan, a vacuum cleaner;
    a recommendation on at least one human action from a group consisting of: to open the window, decrease the number of occupants, leave the place immediately, not to smoke, wear a mask, carry out disinfection and cleaning works, and remove dust; and
    recommendations and potential problems of the parameter ranges where the recommendations and potential problems are a user-friendly interpretation of the obtained values based on the parameter ranges.

4. The environmental monitoring device according to claim 1, wherein average levels of different environmental parameters by the plurality of sensors under their respective measurement periods are obtained.

5. The environmental monitoring device according to claim 1, wherein the real-time air quality report comprises a simultaneous forecast based on average levels of the different environmental parameters to provide an instant average level assessment of at least one environmental parameter not obtained by the plurality of sensors.

6. The environmental monitoring device according to claim 1 wherein air flow rate, heat conduction rate, disperse rate of the pollutants, pollutants emission rate, pollutant removal rate, air-change rate, and other time dependent values, are further assessed and forecasted by the device by at least one of the group consisting of:
    an interrelationship of at least one of an instant level of the obtained environmental parameters and an average level of the obtained environmental parameters;
    an interrelationship of levels of the environmental parameters which are not obtained by the plurality of sensors;
    an interrelationship of the interrelationship of at least one of an instant level of the obtained environmental parameters and an average level of the obtained environmental parameters against a timing factor.

7. The environmental monitoring device according to claim 1, wherein at least one communication input and output port is included in the device and wherein, when a plurality environmental monitoring devices of the same type are connected together with the communication input and output port, trends of at least one of the group consisting of: air flow path, heat conduction path, disperse path of the pollutants, pollutants emission path, pollutant removal path, air-change path is forecasted and displayed in the real-time air quality report.

8. The environmental monitoring device according to claim 1, the user is allowed to setup at least one parameter selected from the group consisting of:
    a measurement period of each sensor;
    a measurement interval for each sensor;
    an operation criteria for each sensor, which based on the obtained values of the environmental parameters of the other sensor;
    a calculation and rule out criteria;
    a number of samplings per sensor and a sampling time per sensor in each measurement period; and
    a number of maximum and minimum sampling values which are to be ruled out during the calculation of the average level of the environmental parameters.

9. The environmental monitoring device according to claim 8, wherein the user sets the device to employ at least one of a normal average calculation for each particular period of measurement and a rolling average calculation for a long term period operation of the device.

10. The environmental monitoring device according to claim 1, wherein a setup performed by the user is performed any time before or during operation of the device; and the setup is stored in the control unit of the device.

11. The environmental monitoring device according to claim 1, wherein the predetermined standards and criteria includes a first judgment principle, where the first judgment principle defining at least two parameter ranges for each environmental parameter, and a corresponding recommendation for each of the at least two parameter ranges.

12. The environmental monitoring device according to claim 11, wherein the predetermined standards and criteria includes a second judgment principle, where the second judgment principle defines at least one conditional array, and the at least two parameter ranges defined by the first judgment principle are used as the parameter ranges for defining each conditional array, and a message corresponding to potential problems for each of the at least one conditional array is provided.

13. The environmental monitoring device according to claim 12, wherein the predetermined standards and criteria includes a third judgment principle, where the third judgment principle defines at least two categories for each environmental parameter and air-quality-level judgment standards for air quality levels are defined based on a combination of different categories of the obtained environmental parameters, and a message corresponding to air quality level by the air-quality-level judgment standards is provided.

14. The environmental monitoring device according to claim 1, wherein the different environmental parameters are selected from a group consisting of: temperature, relative humidity, volatile organic compounds, carbon monoxide, carbon dioxide, dust, ozone, carbon dioxide, air flow rate, radon, and formaldehyde.

15. The environmental monitoring device according to claim 1, further comprises at least one input/output port connected to a central processing unit of at least one air treatment unit, wherein
the central processing units of the at least one air treatment units receive the messages corresponding to the real-time air quality report from the device and based on the message, establish setting and parameter values for an operating condition of the air treatment unit.

16. The environmental monitoring device according to claim 15, wherein the air treatment at least one of a unit and module of air equipment containing containing at least one component selected from a group consisting of: a fan, a blower, a pump, a drawer, a filtration apparatus, a filter for at least one particular type of air pollutant, an apparatus for sterilizing the air, an apparatus for environmental humidity controlling, an apparatus for the environmental temperature controlling, an apparatus for environmental air flow controlling, and an apparatus for controlling environmental brightness.

17. The environmental monitoring device according to claim 15, wherein the setting and parameter values for the operating condition of the air treatment unit based on the messages corresponding to the real-time air quality report controls at least one of a group consisting of:
at least one of an operating time, an air flow rate, an air flow path, and an on and off of an air treatment unit;
at least one of an on and off, and a temperature setting of the apparatus for environmental humidity controlling;
at least one of an on and off, and a temperature setting of the apparatus for environmental temperature controlling; and
at least one of an on and off, and a power setting for an apparatus for sterilizing the air.

18. The environmental monitoring device according to claim 1, wherein the environmental monitoring device is a part of a component which is being included in at least one of an unit and a module of the air equipment containing at least one component selected from a group of components consisting of: a fan, a blower, a pump, a drawer, a filtration apparatus, a filter for at least one type of air pollutant, an apparatus for sterilizing the air, an apparatus for environmental humidity controlling, an apparatus for environmental temperature controlling, an apparatus for environmental air flow controlling, and an apparatus for controlling environmental brightness.

19. The environmental monitoring device according to claim 1, wherein the control unit comprises:
a power supply;
a control circuit;
an input circuit;
an output circuit;
a central processing unit; and
a memory to store the predetermined standards and criteria for judging the environmental parameters, messages corresponding to interpretations, recommendations and potential problems of parameter ranges;
where:
the power supply and the control circuit connect an external power supply to the device;
the input circuit collects the obtained values from the sensors and outputs the obtained values to the central processing unit; and
the central processing unit analyzes the obtained values based on the predetermined standards and criteria and defines the parameter ranges of each environmental parameter, and outputs the interpretation and recommendation of each parameter range for display by the display unit.

20. An environmental monitoring method performed by an environmental monitoring device, comprising:
obtaining values of environmental parameters;
comparing the obtained values of the environmental parameters against predetermined standards and criteria which define parameter ranges of the different environmental parameters in a control unit;
displaying a real-time air quality report from a control unit comprising a simultaneous forecast to provide an instant level assessment of at least one environmental parameter not obtained by the plurality of sensors; and
performing real-time analysis of the obtained values of the different environmental parameters by considering the interrelationship of the obtained values of the different environmental parameters in order to interpret the obtained values and make recommendations based on the obtained values.

21. The environmental monitoring method according to claim 20, wherein the displaying of the real-time air quality report comprises providing the real-time air quality report that includes a simultaneous forecast to provide an instant level assessment of at least one environmental parameter not obtained by the plurality of sensors including at least one selected from the group consisting of: carbon dioxide, carbon monoxide, respirable suspended particulates, ozone, air flow rate, fungi level, total volatile organic compounds, temperature, relative humidity, dew point, air pressure, wind speed, overall air quality, formaldehyde, airborne bacteria, radon, and nitrogen monoxide.

22. The environmental monitoring method according to claim 20, wherein the displaying of the real-time quality report includes providing the real-time air quality report with a user-friendly interpretation of the obtained values based on the parameter ranges comprising at least one selected from the following group consisting of:
a comment on at least one condition selected from a group consisting of: conditions of the air exhausting conditions, an operation condition of the air filtration device, sources which irritate eyes, a respiration system, a number of the of indoor occupants, and messages corresponding to interpretations;
a recommendation on operation of at least one piece of equipment selected from a group consisting of: an air exhausting system, a humidifier, a dehumidifier, an air warming device, an air cooling device, an air filtration device, an combustion oven, a combustion device, a ventilation fan, and a vacuum cleaner; and/or a recommendation for at least one of human action selected from a group consisting of: to open a window, decrease a number of occupants, leave a place immediately, not to smoke, wear a mask, carry out disinfection and cleaning works, and remove dust; and recommendations and potential problems of the parameter ranges.

23. The environmental monitoring method according to claim 20, wherein the predetermined standards and criteria include a first, second and third judgment principle, where the first judgment principle defines parameter ranges for the environmental parameters, the second judgment principle define conditional arrays and at least two parameter ranges defined by the first judgment principle are used as parameter ranges for defining each conditional array, the third judgment principle defining at least two categories for each environmental parameter, and air-quality-level judgment standards for air quality levels are defined based on the combination of different categories of the obtained values, and the method further comprises providing a message corresponding to air quality level by the air-quality-level judgment standards is provided.

24. The environmental monitoring method according to claim 23, further comprising: determining when the at least two parameter ranges of the first judgment principle of one of the conditional arrays of the second judgment principle reach preset values ignoring the at least two parameter ranges of another first judgment principle which was originally consider by the one of the conditional arrays; and shifting to another conditional array.

25. The environmental monitoring method according to claim 24, further comprising turning off the sensor for obtaining the environment values for the at least two parameter ranges of the another first judgment principle when the parameter ranges of the another first judgment principle which was originally considered by the same conditional array become ignored; and reactivating the sensor will when the values of the parameter ranges being re-considered at the time the parameter ranges of first judgment principle of the conditional array returned to original defined ranges.

* * * * *